United States Patent [19]
England et al.

[11] Patent Number: 5,466,530
[45] Date of Patent: Nov. 14, 1995

[54] BIOCOMPATIBLE COMPONENTS FABRICATED FROM A SUBSTANTIALLY CONSOLIDATED STOCK OF MATERIAL

[76] Inventors: Garry L. England, Winona Lake; Joel C. Higgins, Claypool, both of Ind.

[21] Appl. No.: 6,747

[22] Filed: Jan. 21, 1993

[51] Int. Cl.$^6$ .................................................. B32B 27/32
[52] U.S. Cl. ........................................ 428/411.1; 428/500
[58] Field of Search ............................... 428/411.1, 500; 264/126, 162; 425/405.2

[56] References Cited

U.S. PATENT DOCUMENTS

| | | | |
|---|---|---|---|
| 4,187,210 | 2/1980 | Howard, Jr. | 260/42.14 |
| 4,587,163 | 5/1986 | Zachariades | 428/292 |
| 5,030,402 | 7/1991 | Zachariades | 264/138 |
| 5,037,928 | 8/1991 | Li et al. | 526/352 |
| 5,210,130 | 5/1993 | Howard, Jr. | 524/789 |

OTHER PUBLICATIONS

"Hot Isostatic Pressing: Gets Bigger, Hotter and More Flexible", *Carbide & Tool*, vol. 19, No. 2, May–Jun. 1987.
"High Performance Ceramics, the future materials–available today", *AAB Cerama AB* brochure, May 1988.
"Automated IsoPress", *ABB Autoclave Systems, Inc.*, Technical Bulletin 5319 (pre–Jan. 21, 1992).
"Isostatic Pressing: Stating the Art", *Tooling & Production*, v. 48, p. 43, Dec. 1982.
"CP3–60: Cold Isostatic Press", ISO–Spectrum Inc. brochure (pre–Jan. 21–1992).
"HP6–30: Hot Isostatic Press", ISO–Spectrum Inc. brochure (pre–Jan. 21, 1992).
Price, P., and Kohler, S., "Hot Isostatic Pressing of Metal Powders", *Metal Handbook*, pp. 419–443, 1983.
Price, P., and Kohler, S., "Cold Isostatic Pressing of Metal Powders", *Metal Handbook*, pp. 444–450, 1983.

*Primary Examiner*—Paul J. Thibodeau
*Assistant Examiner*—David Abraham
*Attorney, Agent, or Firm*—Harness, Dickey & Pierce

[57] ABSTRACT

A method for forming biocompatible components from a stock of substantially completely consolidated material. The method includes the step of forming an incompletely consolidated stock from a powder. The substantially completely consolidated stock is then formed from the incompletely consolidated stock. Finally, the substantially completely consolidated stock is then machined to form the biocompatible component.

6 Claims, 4 Drawing Sheets

BIOCOMPATIBLE COMPONENTS FABRICATED FROM A SUBSTANTIALLY CONSOLIDATED STOCK OF MATERIAL

BACKGROUND OF THE INVENTION

The present invention relates generally to biomedical implant devices, and more particularly to a method for forming biocompatible components.

A natural joint in the human body such as a knee joint may undergo degenerative changes due to a variety of etiologies. When these degenerative changes become advanced and are irreversible, it may ultimately become necessary to replace the natural joint with a prosthetic joint. Such a prosthetic joint often includes several biocompatible components which are formed from high strength synthetic materials. These materials are not only able to accommodate the various loading conditions that the prosthetic joint may encounter, but are also biocompatible with the human body. An example of such high strength synthetic materials is ultra-high molecular weight polyethylene which is often used when there is relative movement between the adjacent metallic surface of a prosthetic joint.

Biocompatible components which are made from ultra-high molecular weight polyethylene are often formed using one of two different techniques. In one technique, a relatively precise amount of polyethylene powder is placed between two halves of a die which are then simultaneously compressed and heated. After the powder is densified using standard sintering techniques, the die is allowed to cool. The biocompatible component is then removed from the die and is sterilized in a manner well-known to those skilled in the art.

In the second technique, a substantially completely consolidated polyethylene stock is first formed and then the biocompatible component is machined from the substantially completely consolidated stock. Several methods exist which may be used to form the substantially completely consolidated stock. In one method, the substantially completely consolidated stock is extruded by placing polyethylene powder in a cylindrical chamber having an opening of a particular shape at one end of the chamber. A hydraulically operated piston located at the other end of the cylinder is then used to compress the polyethylene powder. The force exerted by the piston on the polyethylene powder causes the powder to compact. Heat is also applied to solidify the powder as it moves through the cylinder. In another method for forming a substantially completely consolidated stock, polyethylene powder is placed between two flat plates which are compressed while heat is applied. As this occurs, the polyethylene powder is densified so as to form the substantially completely consolidated stock.

While these two techniques for forming biocompatible components are effective, they nevertheless have certain disadvantages. With respect to the first technique described above, it will be appreciated that only one biocompatible component can be made at one time. Accordingly, this technique is relatively inefficient in terms of the amount of time required to make the biocompatible component. With respect to the second technique in which the biocompatible component is formed from a substantially completely consolidated stock, the resulting consolidated stock may often require a stress relief operation or an annealing operation prior to machining. In addition, when polyethylene stock is formed by heating polyethylene powder between two plates acting under pressure, the resulting may have density gradients or voids due to the relatively nonuniform pressure applied to the powder across the plates.

In addition, methods are also known for treating ultrahigh molecular weight polyethylene prior to being machined into a biocompatible component. One such method is disclosed in U.S. Pat. No. 5,037,928. However, during the procedure described in this reference, the polyethylene stock is placed under a sufficient pressure so as to induce pressure crystallization of the stock. This pressure crystallization tends to cause increased susceptibility to wear. In addition, the use of this relatively high pressure required that relatively expensive pressure containment vessels be used. Furthermore, this method describes processing preformed polyethylene stock which often has unwanted density gradients or voids as described above.

SUMMARY OF THE INVENTION

An advantage of the present invention is to provide a method for forming biocompatible components using a multiple-step technique which can produce biocompatible components relatively quickly at a reduced cost.

A further advantage of the present invention is to provide a method for forming biocompatible components which produces a stock of consolidated ultra-high molecular weight polyethylene which can be machined without being subjected to a stress relief or annealing operation.

Another advantage of the present invention is to provide a method for forming biocompatible components which does not substantially increase the crystallization of the stock used to form the biocompatible component.

A further advantage of the present invention is to provide a method for forming biocompatible components which uses both a cold isostatic pressure treatment as well as a hot isostatic pressure treatment.

A further advantage of the present invention is to provide a method for forming biocompatible components which enhances the bonding between the composite materials from which the biocompatible component is made.

A further advantage of the present invention is to provide a method for forming biocompatible components which facilitates the adhesion of a porous metal coating.

In one form thereof, the present invention provides a method for forming biocompatible components from a powder such as ultra-high molecular weight polyethylene. The method includes enclosing the powder in a first container and subjecting the first container to a cold isostatic pressure treatment which forms an incompletely consolidated stock from the powder. The incompletely consolidated stock is removed from the first container and is placed in a second container which is then located within a hot isostatic press and is subjected to a hot isostatic pressure treatment. The hot isostatic press treatment forms the relatively completely consolidated stock from the incompletely consolidated stock. The relatively completely consolidated stock is then machined into a biocompatible component.

DETAILED DESCRIPTION OF THE PREFERRED EMBODIMENT

It should be understood that while this invention is described in connection with a particular example thereof, the scope of the invention need not be so limited. Rather, those skilled in the art will appreciate that the following teachings can be used in a much wider variety of applications than the examples specifically mentioned herein.

Figures 1, 2, 3:
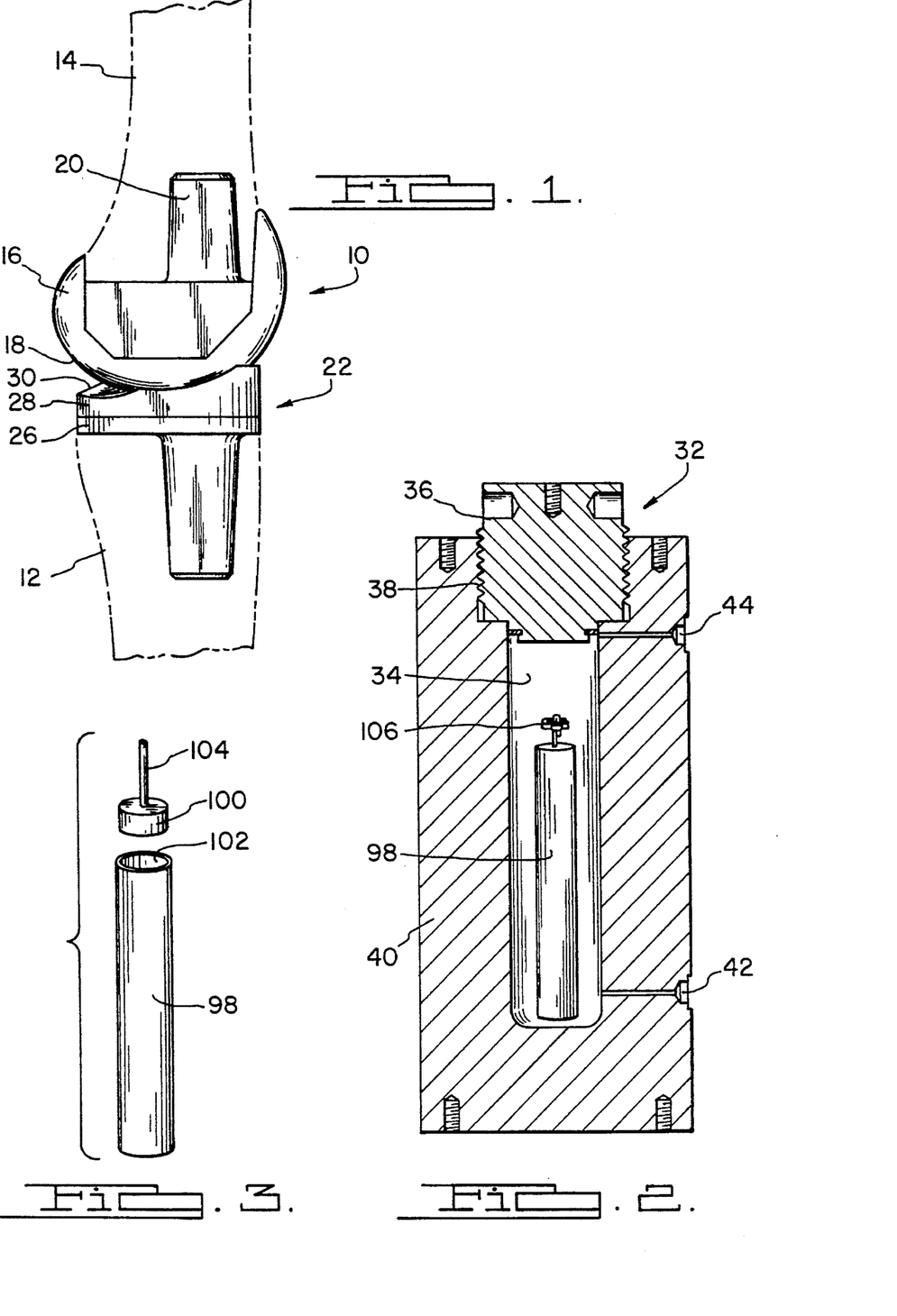
FIG. 1 is a sagittal elevational view of a knee joint prosthesis including a biocompatible component in the form of a tibial bearing formed from ultra-high molecular weight polyethylene by the preferred embodiment of the present invention.
FIG. 2 is a cross-sectional view of a cold isostatic press of the type used in accordance with the teachings of the preferred embodiment of the present invention.
FIG. 3 is a perspective view of the first container used with the cold isostatic press shown in FIG. 2 according to the preferred embodiment of the present invention.

Referring now to FIG. 1, a knee joint prosthesis is shown which is generally designated by the numeral 10. The knee joint prosthesis 10 is functionally depicted as being secured to a tibia 12 and a femur 14 of a surgically resected knee joint, with the tibia 12 and femur 14 being shown in phantom. The knee joint prosthesis 10 is shown to include a femoral component 16 having a bearing surface 18. The femoral component 16 is secured to the femur 14 by means of an inferiorly extending femoral stem 20 inserted into a matching bore created within the femur 14 in a manner well-known to those skilled in the art.

The knee joint prosthesis 10 is further shown to include a tibial component 22 that is secured to the tibia 12 by means of an interiorly extending tibial stem 24 inserted into a matching bore created within the tibia 12 in a similar manner as that described above. The tibial component 22 includes a platform-like tibial tray 26 which is used to support a tibial bearing 28 constructed by the method of the present invention. The tibial bearing 28 is formed to be symmetrically oriented about the sagittal plane. In operation, the tibial bearing 28 provides a bearing surface 30 that is operable to accept a rotatable, low friction contact relationship with the bearing surface 18 of the femoral component 16.

The tibial bearing 28 is formed of a low friction material having enhanced wear resistance properties. In a preferred embodiment, the tibial bearing 28 is machined from a substantially completely consolidated stock that is molded from an ultra-high molecular weight polyethylene powder having a molecular weight of from about 3 million to about 6 million. The ultra-high molecular weight polyethylene powder may be any powder conforming to ASTM F-648, though preferable powders include Hifax 1900 resin available from Himont and GUR 405 or 415 resin available from Hoechst Celanese. It will be understood, however, that other suitable materials may be used to form a stock from which a tibial bearing 28 may be machined. For example, the formation of articles from this method can be accomplished using other polymer materials in powder form, preferably having a molecular weight of from about 3 million to about 6 million. The specific method used to form the tibial bearing 28 includes several steps which are more fully described below. However, several of these steps involve the use of either a cold isostatic press or a hot isostatic press. Accordingly, the structure and operation of the cold isostatic press and the hot isostatic press will now be described.

Referring to FIG. 2, a cold isostatic press 32 according to the preferred embodiment of the present invention is shown which includes a pressure chamber 34 that has an upper cover 36. The upper cover 36 includes a threaded closure 38 that enhances a sealed condition within the pressure chamber 34 when the pressure chamber 34 is pressurized. When the pressure chamber 34 is sealed in this manner, the length of the pressure chamber 34 is approximately 24–30 inches and the diameter of the pressure chamber 34 is approximately 12 inches. The pressure chamber 34 is substantially surrounded by an annular wall 40 which is operable to define the pressure chamber 34, and has a thickness which is sufficient to contain the pressure within the pressure chamber 34.

The cold isostatic press 32 further includes a pressure inlet line 42 and a pressure relief line 44. The pressure inlet line 42 and pressure relief line 44 are preferably tubular passageways each regulated by a pressure control mechanism (not shown) that are operable to accommodate a pressurized transfer of a gas or liquid fluid from an external source (not shown) into and out of the pressure chamber 34.

The cold isostatic press 32 is preferably designed to operate at pressures capable of compacting the powder to about 60–80% of its desired final density, with the preferable range being between 65–75%. The cold isostatic press 32 may be that which is available from National Forge, Andover, Mass. or Models IP6-24-60 and IP8-36-60 which are available from ABB Autoclave Systems, Inc. of Columbus, Ohio. However, other suitable cold isostatic presses may be used.

The hot isostatic press 46 will now be described with reference to FIG. 3. The hot isostatic press 46 is shown to include a pressure chamber 48 which is defined in part by an annular wall 50, the thickness of which is between about 6 inches and about 3 inches. In addition, the pressure chamber 48 is about 18 inches in diameter and is about 53 inches in length. The hot isostatic press 46 further includes a lower closure 52 and upper closure 54 which are threadedly attached to the annular wall 50 by matching buttress threads 56 and 58. It is to be understood, however, that a pin locking mechanism may also be employed for securing the lower closure 52 and upper closure 54 to the annular wall 50. The lower closure 52 and upper closure 54 are operable to maintain a heated and pressurized condition within the pressure chamber 48 during the hot isostatic pressure treatment described below.

The hot isostatic press 46 further includes a plurality of heating elements 60 that are operable to generate thermal energy within the pressure chamber 48. Alternatively, the hot isostatic press 46 may include another heating means, such as a solution jacket adjacent to the pressure chamber 48, that is operable to contain a hot fluid for providing thermal energy to the pressure chamber 48. The hot isostatic press 46 is also shown to include a cooling jacket 62 which comprises a plurality of coils encircling the annular wall 50. The cooling jacket 62 is operable to contain a suitable heat transfer fluid for removing thermal energy from the hot isostatic press 46 by a transfer of thermal energy into the cooling fluid. It will be understood, however, that the cooling function accomplished by the cooling jacket 62 can be performed by another cooling means disposed at a different location within the hot isostatic press 46, such as within the pressure chamber 48 or between the pressure chamber 48 and the annular wall 50.

The hot isostatic press 46 further includes a heat shield 64 which is located between the annular wall 50 and the heating elements 60. The heat shield 64 is operable to limit heat losses from within the pressure chamber 48 and to assist in controlling the temperature within the pressure chamber 48. The hot isostatic press 46 also includes a pressure system (not shown) of a type well-known to those skilled in the art that is operable to pressurize the pressure chamber 48. The pressure system also communicates with the pressure chamber 48 by means of a pressure input/output line 68 that is connected to an inert gas source and compressor of a type well-known to those skilled in the art. In a preferred embodiment, the inert gas is argon, though nitrogen, helium and neon gases may also be used.

The hot isostatic press 46 further includes a power distribution system (not shown) of a type well-known to those skilled in the art. The power distribution system is used for controlling the heat and pressure within the pressure chamber 48. In addition, the electrical energy required by the heating elements 60 is provided in this embodiment by an electrical power line 72 that is connected to an electrical power source (not shown).

The hot isostatic press 46 is operable to change the temperature within the pressure chamber 48 from an initial room temperature of from about 60° F. to about 70° F. to an operating temperature of from about 365° F. to about 420° F. In addition, the hot isostatic press 46 is also operable to change the pressure within the pressure chamber 48 from approximately atmospheric pressure to an operating pressure of preferably from about 7,500 pounds per square inch to about 10,000 pounds per square inch. The hot isostatic press 46 may be one of several well-known to those skilled in the art, such as Model HP6-30, available from Iso-Spectrum, Inc. of Columbus, Ohio. Other suitable hot isostatic presses are available from National Forge of Andover, Mass. However, other suitable hot isostatic presses may be used.

Figure 4:
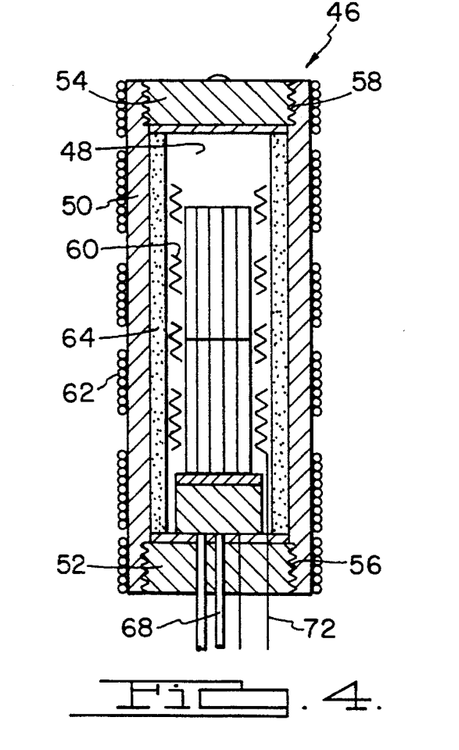
FIG. 4 is a cross-sectional view of a hot isostatic press of the type used in accordance with the teachings of the preferred embodiment of the present invention.

The method of the preferred embodiment of the present invention will now be described with reference to FIG. 4 which comprises the steps 80 through 96. At step 80, an ultra-high molecular weight polyethylene powder is introduced into a first container 98 (see FIG. 3) so as to substantially fill the first container 98. The first container 98 is preferably both flexible and collapsible, and is made from a material that has sufficient strength to contain the powder over the operating pressure ranges during the cold isostatic pressure treatment without exhibiting any physical deterioration, chemical degradation or chemical interaction with the powder disposed therein. It is also preferred that the first container 98 be made of a material that will not adhere to the powder at any time during the cold isostatic pressure treatment.

In a preferred embodiment, the first container 98 is a cylindrical polyurethane container of dimensions approximately inches in diameter, 18 inches in length, and has a wall thickness of approximately one-half inch to three-fourths inch. The first container 98 is sealed by means of a plug 100 that is inserted into a matching port 102 at one end of the first container 98. The plug 100 is secured to the first container 98 by means of an adhesive, such as a hot melt glue, located on the top of the interface of the plug 100 and the matching port 102. Because it is desirable that the first container 98 be substantially evacuated prior to the cold isostatic pressure treatment, the plug 100 of the first container 98 preferably includes an evacuation/de-airing tube 104. The evacuation/deairing tube 104 is operable to be connected to an evacuation pump (not shown) and subsequently sealed by any suitable means prior to the cold isostatic pressure treatment.

It will be noted that the size and shape of the first container 98 will vary depending upon the desired size and shape of the consolidated stock being formed. It will also be noted that other suitable materials may be used to form the first container 98 and that other suitable means may be used for substantially sealing and evacuating the first container 98. For example, a flexible and collapsible rubber material may be employed for constructing the first container 98. When constructed of polyurethane, the first container 98 may be reused provided it is not subjected to extended periods of high temperature.

Once the first container 98 has been filled with powder, the first container 98 is sealed in the manner described above. The first container 98 is then substantially evacuated and then the evacuation/de-airing tube 104 is sealed by any suitable means such as by a clamp 106. As is illustrated by the step 82, the first container 98 is then located within the pressure chamber 34 of the cold isostatic press 32. The pressure chamber 34 is substantially sealed at step 84 to enclose the first container 98 by threading the upper cover 36 onto the matching threads 38 disposed upon the annular wall 40.

The first container 98 is then subjected to a cold isostatic pressure treatment as indicated by the step 86 during which a uniform pressure is applied to the first container 98. In this regard, the pressure applied to the first container 98 is developed by introducing a pressurized fluid into the pressure chamber 34. This pressurized fluid may be water, mineral oil or other oils having similar compressive properties, as well as inert gases such as argon, nitrogen, helium and neon. In addition, the pressure chamber 34 may be partially filled with water while the pressurized gas may be used to fill the remainder of the pressure chamber 34. The pressure within the pressure chamber 34 is preferably increased as quickly as possible from approximately atmospheric pressure to a pressure sufficient to form the powder into an incompletely consolidated stock that can be manipulable for further processing without substantial degradation. Suitable maximum pressures range from 1100 psi to 10,000 psi which are generally sufficient to compact the powder to 60–80% of its final density. Below this range the incompletely consolidated stock is structurally unstable and above this range gases may become trapped within the incompletely consolidated stock during evacuation of the first container 98. In a preferred embodiment, the maximum pressure applied to the first container 98 is approximately 1500 psi, and the typical length of time for increasing the pressure to this level may be approximately 2 to 5 minutes. However, maximum pressure applied to the first container 98 is dependent upon several factors including the size of the first container 98, the amount of powder within the first container 98, the size of the resulting stock needed to manufacture the tibial bearing 28 and the size of the pressure chamber 34. The pressure is preferably held at the maximum pressure for approximately one minute, though longer times can be used.

After the maximum pressure within the cold isostatic press 32 is maintained for approximately one minute, the pressure is slowly reduced so as to allow the resulting incompletely consolidated stock to relax within the first container 98 without yielding to outward internal pressure which can cause the incompletely consolidated stock to lose integrity. The pressure is preferably released over a period of from approximately 10 to approximately 30 minutes, although longer times can be used.

The cold isostatic press treatment enhances a uniform density within the incompletely consolidated stock and reduces internal stresses from appearing within the material being formed during the subsequent hot isostatic pressure treatment. In addition, the shape of the incompletely consolidated stock is in large part dependent upon the shape of the first container 98. The incompletely consolidated stock resulting from the cold isostatic press treatment is typically compacted to a preferred density of about 70% of its desired final density following the hot isostatic pressure treatment.

After the incompletely consolidated stock has been removed from the first container 98, the incompletely consolidated stock is placed in a second container 108 (see FIG. 5) as indicated by the step 88. The second container 108 is preferably a collapsible container made from a material that has sufficient strength to contain the incompletely consolidated stock over the temperature and pressure ranges encountered in the hot isostatic press treatment without exhibiting any physical deterioration, chemical degradation or chemical interaction with the incompletely consolidated stock. It is also preferred that the second container 108 be made of a material that will not adhere to the incompletely consolidated stock at any time during the hot isostatic pressure treatment. In a preferred embodiment, the second container 108 is a foilized heat sealable bag that has an external surface formed from a layer of an aluminum foil with a polyester vapor barrier, and has an internal surface formed from a heat-sealable, low density polyethylene layer on its internal surface. The second container 108 may typically be approximately 18 inches in length, approximately 12 inches in width and have a wall thickness of between approximately 2–3 mils. As will be appreciated by those skilled in the art, the second container 108 may be made from other suitable materials as well.

Figure 5:
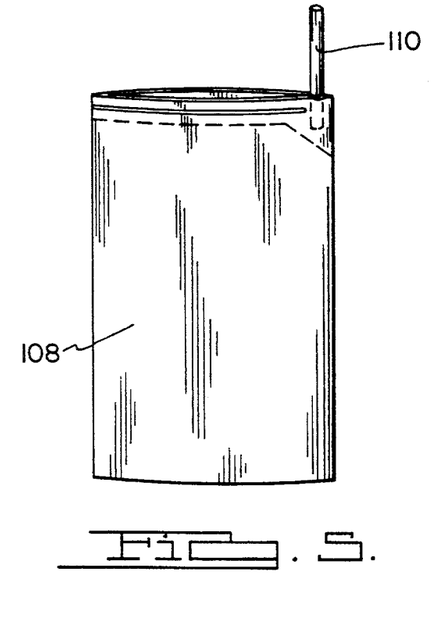
FIG. 5 of the second container used in conjunction with the hot isostatic press shown in FIG. 4 according to the preferred embodiment of the present invention.
Figure 6:
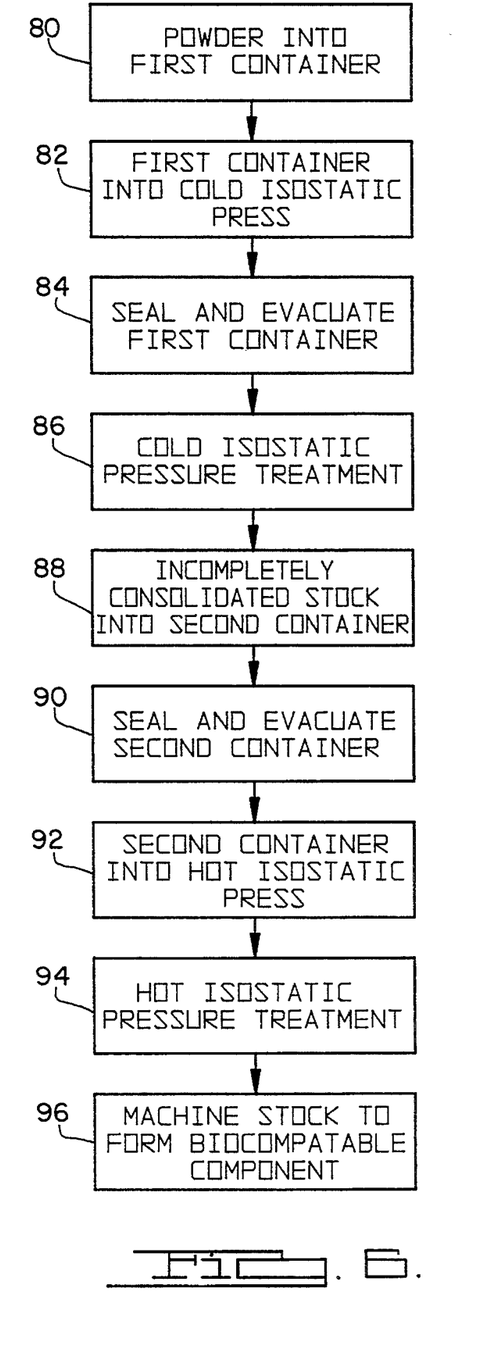
FIG. 6 is a flow diagram illustrating the steps for forming a biocompatible component according to the preferred embodiment of the present invention.

Because it is desirable to have the second container 108 be substantially evacuated prior to the hot isostatic pressure treatment, the second container 108 preferably includes an evacuation tube 110 that is operable to be connected to a vacuum pump (not shown). In this regard, the evacuation tube 110 is placed in the second container 108 and then a heat sealer is used to seal that region of the second container 108 which is not immediately adjacent to the evacuation tube 110. Hot melt glue is then placed around the region of the second container 108 which is adjacent to the evacuation tube 110.

It will be noted that the size and shape of the second container 108 will vary depending upon the desired size and shape of the consolidated stock being formed. It will also be noted that other suitable materials may be used for the second container 108 and that other suitable means may be used for sealing and evacuating the second container 108.

After the incompletely consolidated stock is placed in the second container 108, the second container 108 is evacuated in similar fashion to the evacuation of the first container 98 as indicated by the step 90. A heat sealer is then used to substantially enclose the second container 108 at a region below the evacuation tube 110. The evacuation tube 110 may then be removed from the second container 108.

Once the incompletely consolidated stock is placed within the second container 108 and the second container 108 is sealed and evacuated. The second container 108 is then placed into the pressure chamber 48 of the hot isostatic press 46 as indicated by the step 92 of the present invention. The lower closure 52 and the upper closure 54 of the hot isostatic press 46 are then closed to substantially enclose the second container 108 within the hot isostatic press 46.

At step 94, the incompletely consolidated stock undergoes the hot isostatic pressure treatment. In this regard, the pressure within the pressure chamber 48 is initially raised to approximately 24 psi while the temperature of the hot isostatic press 46 is raised between 365° F. and 420° F. Below this range the incompletely consolidate stock does not melt and above this range the polyethylene may degrade. Preferably, the temperature of the hot isostatic press is raised to between 365°– 385° F. to minimize the possibility that degradation will occur. Most preferably, the temperature is raised to 365° F. Once 365° C. is reached, the temperature of the hot isostatic press 46 is raised as quickly as possible and may typically heat between one to three hours.

When the temperature of the hot isostatic press 46 reaches approximately 365° C. the pressure within the pressure vessel 46 is also increased over a 1–2 hours period to a pressure preferably between about 7,500 to about 10,000 psi. It will be appreciated that the maximum pressure may range from about 3,000 psi to about 40,000 psi. However, pressures below 3,000 psi or above 40,000 psi tend to cause consolidation errors to occur or may cause the resulting completely consolidated stock to have an undesirable crystalline structure. The preferred maximum pressure between 7,500 psi and 10,000 psi is dependent upon several factors including the size, shape and construction of the second container, the dimensions of the pressure chamber 48 and the desired final diameter of the resulting completely consolidated stock. In addition, the duration of the hot isostatic pressure treatment may also depend on the size of the resulting completely consolidated stock. For example, smaller diameters of the completely consolidated stock (e.g., 1½ inches) typically require less time to become fully compacted, while larger diameters of completely consolidated stock, such as 4 inches, typically require more time to become fully cured. In addition, the use of the lowest satisfactory pressure is desirable as it would tend to prolong equipment life. An inert gas such as argon is preferably used in the hot isostatic press 46 as the pressure medium. Alternative selections for the pressure medium include nitrogen, helium and neon gases, although these gases can be chemically reactive under certain conditions.

Once the temperature and pressure have reached the desired levels, the temperature and pressure of the pressure chamber 48 remains relatively constant for a given dwell time. During this dwell time, the powder is further compressed so as to minimize any compression release that may occur following termination of the application of heat and pressure. Preferred dwell times are dependent upon the desired final diameter of the consolidated stock being produced, and range from approximately 45 minutes to several hours or more. For example, typical desired dwell times may be approximately 45 minutes to approximately 1 hour for a 1 inch diameter consolidated stock, approximately 2 hours for a 2½ inch diameter consolidated stock, and approximately 5 hours for a 4 inch diameter consolidated stock.

After the second container 108 has been subjected to the desired temperature and pressure for the given dwell time, the hot isostatic press 46 is allowed to cool to room temperature. After the temperature of the hot isostatic press 46 cools to approximately 100° F., the pressure within the pressure chamber 48 is gradually decreased to approximately atmospheric pressure over a period of time that is dependent upon the desired final diameter of the consolidated stock being produced. In this regard, the pressure for larger diameters of consolidated stock may be reduced more slowly because they may typically have a larger internal compression and larger potential energy that are more likely to release upon removal of pressure. For example, a 1 hour pressure release time is preferred for a 4 inch diameter consolidated stock, while a 20 minute pressure release time may be sufficient for a 1½ inch diameter consolidated stock. After the release time has elapsed, the pressure chamber 48 is then opened and the second container 108 is removed from the pressure chamber 48.

The consolidated stock is removed from the second container 108 and is machined at step 96 under methods well-known to those skilled in the art to produce the desired product, such as the tibial bearing 28, acetabular cup replacement or other biocompatible component. After machining the consolidated stock at step 92 to form the tibial bearing 28, the tibial bearing 28 is then sterilized in a manner well-known to those skilled in the art.

Figure 7:
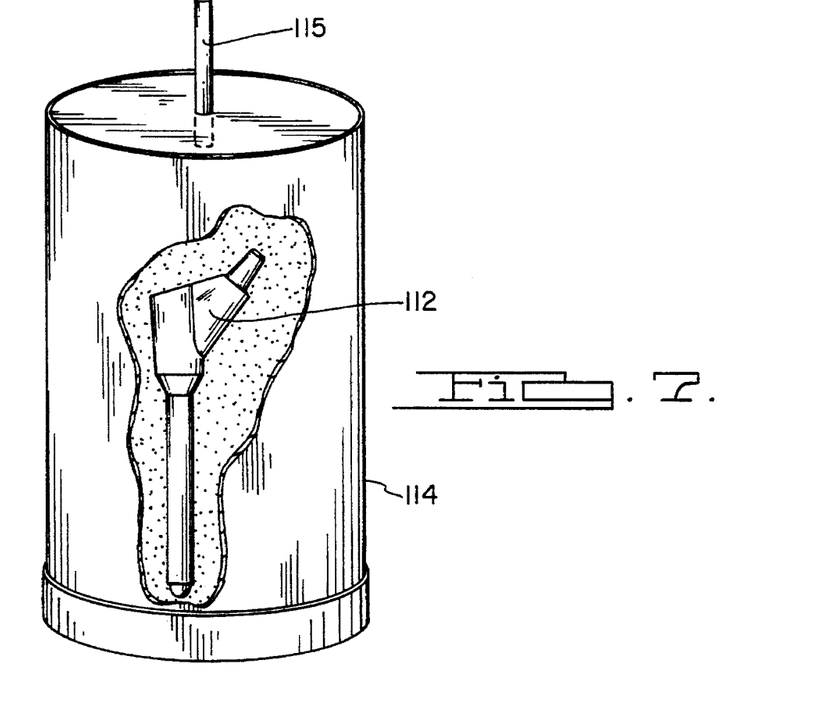
FIG. 7 is a perspective view of the container which is used in accordance with the preferred embodiment of the present invention to enhance binding of the layers of composite material of a biocompatible component.

In addition to using of the hot isostatic press 46 in forming a completely consolidated stock, the hot isostatic press 46 may be also used to enhance the adhesion between materials which form a composite biocompatible component. For example, as shown in FIG. 7, a biocompatible component 112 representing a femoral hip stem of a hip joint prosthesis is shown. The biocompatible component 112 is preferably formed of a biocompatible thermoplastic having a biocompatible fibrous material disposed therein. The biocompatible thermoplastic may be polysulfone, poly ether ether ketone (PEEK), or poly aryl ether ketone (PAEK), though other suitable materials may be used. The amount and orientation of the biocompatible fibrous material within the biocompatible component 112 is selected to achieve the desired structural modulus for the biocompatible component. The biocompatible fibrous material may be either continuous or chopped fibers, though other suitable materials may be used.

When used in this manner, a sheet of the biocompatible thermoplastic such as polysulfone is first formed into two portions, each portion having a shape generally corresponding to one-half of the biocompatible component 112. Each portion of the biocompatible thermoplastic is then placed within the container 114 with the biocompatible fibrous material disposed between the portions. The container 114 is preferably made from copper or stainless steel. However, other suitable materials such as high temperature silicon, which does adhere to the polysulfone, may also be used. The container 114 is then filled with zirconium oxide beads (i.e., $Zr_2O_3$) and is then evacuated using the evacuation tube 115 which is then sealed. It will be appreciated that zirconium oxide beads do not have to be used when the container 114 is made from a very pliable material such as high temperature silicon. The container 114 is then placed in the hot isostatic press 46 and is subjected to the hot isostatic pressure treatment in a manner similar to that described above. In this regard, the maximum temperature of the isostatic pressure treatment is preferably slightly above the melting temperature of the biocompatible thermoplastic. In addition, the pressure applied and the duration of the hot isostatic pressure treatment should be sufficient to cause the biocompatible thermoplastic to encapsulate the biocompatible fibrous material. Preferably, the temperature will fall within the range of 400°–440° F. while the pressure will be greater than between 5000 psi and 7500 psi, and most preferably greater than 7500 psi. It will be understood by those skilled in the art, however, that the temperature, pressure and duration of the hot isostatic pressure treatment will depend upon the specific materials being used.

Figure 8:
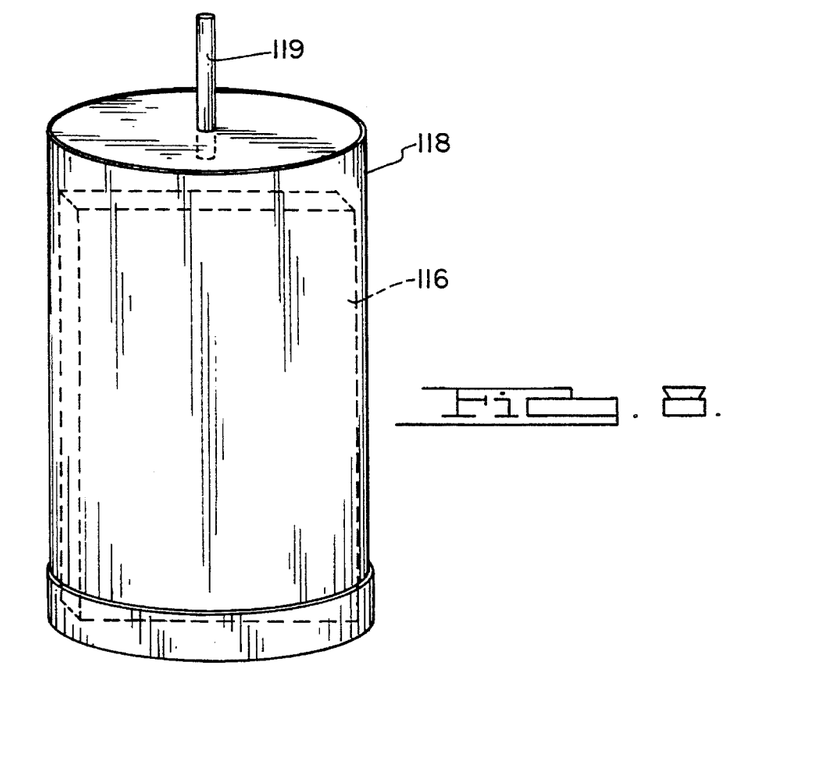
FIG. 8 is a perspective view of the container used in accordance with the preferred embodiment of the present invention to reduce voids in a stock of biocompatible composite material.

The isostatic press 46 may also be used to reduce the voids in a stock of biocompatible composite material prior to being machined into a biocompatible component. For example, as shown in FIG. 8, a biocompatible material stock 116 is shown as being disposed within a container 118. The biocompatible material stock 116 may be made from polysulfone, poly ether ether ketone (PEEK), or poly arly ether ketone (PAEK), though other suitable materials may be used. The container 118 may be a stainless steel or a copper container. However, the container may also be a stainless steel heat treat bag of the type which is available from Sentry Company, Foxboro, Mass., other suitable containers may be used.

When used in this manner, the biocompatible material stock 116 is first placed within the container 118 and then the container 118 is filled with zirconium oxide beads. It will be appreciated, however, that zirconium oxide beads do not have to be used if the container 118 is made from a pliable material such as a heat treat bag. The container 118 is then sealed. A vacuum is then drawn on the container 118 through the evacuation tube 119 and then the evacuation tube 119 is then sealed by closing a valve connected to the evacuation tube 119. The container 118, with the biocompatible stock material 116 located therein, is placed in the isostatic press 46 and the temperature and pressure of the isostatic press 46 are raised to such an extent that the voids formed within the biocompatible stock material 116 are reduced. This reduction in voids occurs because of the external pressure applied to the exterior of the container 118. By using the isostatic press 46 in this manner, the resulting biocompatible material has improved consolidation. The temperature to which the hot isostatic press 46 is raised will be substantially that of the glass transition temperature of the resin of the biocompatible stock material 116, while the pressure applied by the hot isostatic press 46 is as high as reasonably possible. Preferably, the temperature will fall within the range of 400°–440° F. while the pressure will be greater than between 5000 psi and 7500 psi, and most preferably greater than 7500 psi. However, other suitable temperatures and pressures may be used.

Figure 9:
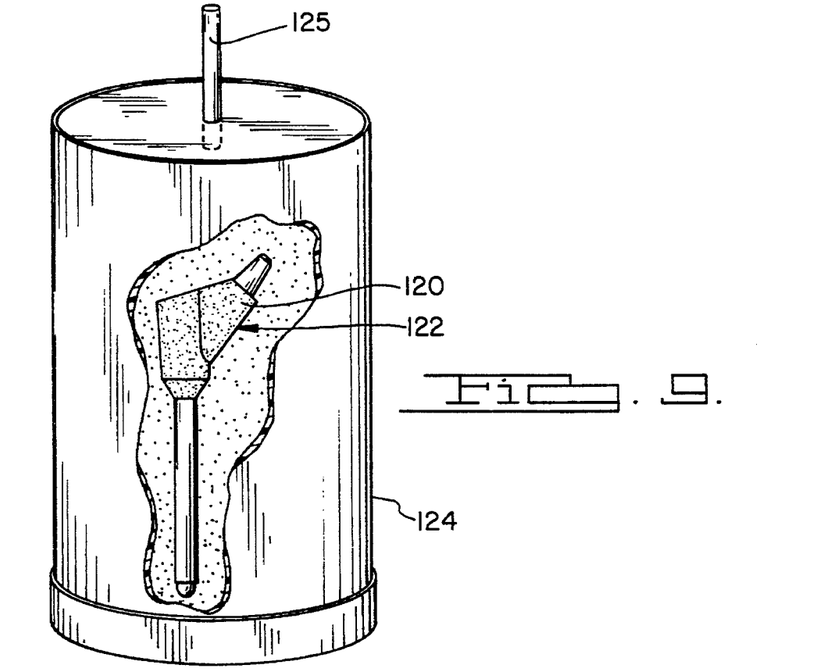
FIG. 9 is a perspective view of the container used in accordance with the preferred embodiment of the present invention to enhance adhesion of a porous coating to a biocompatible component.

The isostatic press 46 may also be used to enhance the adhesion of a porous coating on a biocompatible component formed from a composite material. As shown in FIG. 9, the biocompatible component 120 includes a porous coated surface 122 which is used to facilitate adhesion of the biocompatible component immediately after surgery. The porous coated surface 122 may be applied by a plasma spray operation and may comprise an alloy of Ti-6Al-4V, commercially pure titanium, a cobalt chrome alloy or other biocompatible materials.

When the isostatic press 46 is used to enhance adhesion of a porous coating 122 onto the biocompatible component 120, the porous coated surface 122 is first applied to the biocompatible component 120 by a plasma spray operation.

The biocompatible component 120 is then placed in a container 124 and then the container 124 is filled with zirconium oxide beads. The container 124 is then sealed and then is evacuated through the evacuation tube 125. The container 124 is preferably made of stainless steel or copper. However, other suitable materials such as high temperature silicon, which does not adhere to the component 120 may also be used. It will be appreciated, however, that zirconium oxide beads do not have to be used if the container 124 is made from a pliable material such as high temperature silicon. The container 124, with the biocompatible component 120 inside, is then placed in a hot isostatic press 46 which is then operated in a manner similar to that described above. Preferably, the temperature will fall within the range of 400°–440° F. while the pressure will be greater than between 5000 psi and 7500 psi, and most preferably greater than 7500 psi. As a result, the adhesion of the porous coated surface 122 to the biocompatible component 120 is improved.

Figure 10:
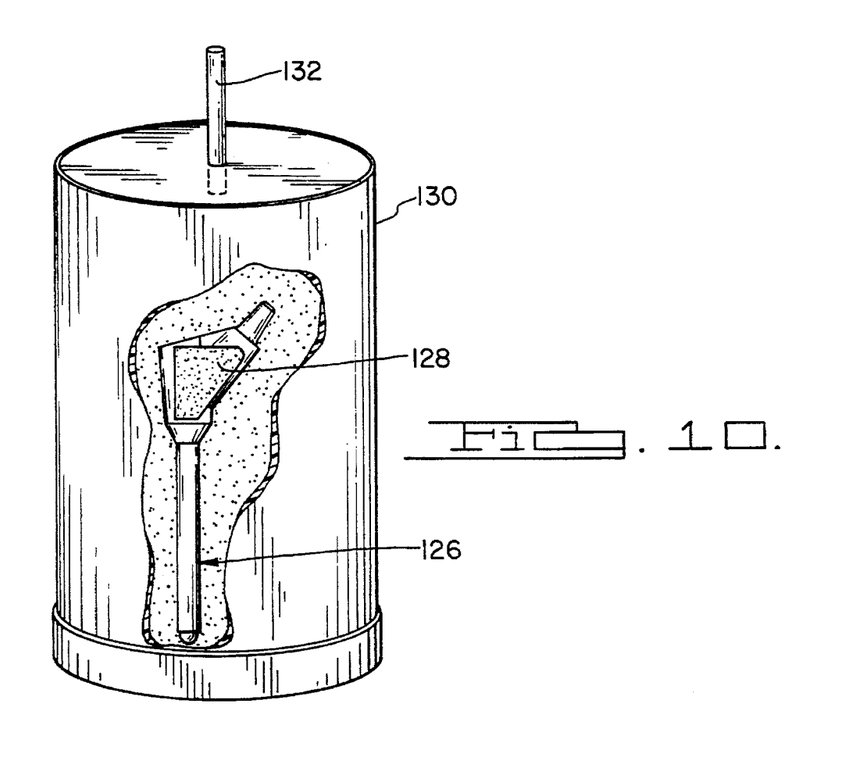
FIG. 10 is a perspective view of the container used in accordance with the preferred embodiment of the present invention to facilitate adhesion of porous coated pads on a biocompatible component.

The hot isostatic press 46 may also be used to enhance adhesion of porous coated pads on a biocompatible component. As shown in FIG. 10, the biocompatible component 126 includes a plurality of porous coated pads 128 which are used to facilitate fixation of the biocompatible component 126 immediately after surgery. The porous coated pads 128 may be made from a titanium alloy such as Ti-6A1-4V, commercially pure titanium, a cobalt chrome alloy or other biocompatible metal alloys. While the porous coating on the porous coated pads 128 may be applied by a flame spray, plasma spray or sputtering techniques, it will be appreciated that other suitable methods may be used.

When the hot isostatic press 46 are used to enhance adhesion of the porous coated pads 128 onto the biocompatible component 126, the regions on the biocompatible component 126 where the porous coated pads 128 are to be placed are first coated with methylene chloride to partially dissolve those regions at the biocompatible component 126. The porous coated pads 128 are then applied to the biocompatible component 126 and are temporarily secured thereto. The biocompatible component 126, together with the porous coated pads 128, are then placed in the container 130 and then the container 130 is filled with zirconium oxide beads. The container may be made from stainless steel or copper, though other suitable materials may be used. In this regard, pliable materials such as high temperature silicon which is able to withstand the operating temperatures and pressures may be used which do not necessarily require the use of zirconium oxide beads. After the container 130 is evacuated through the evacuation tube 132 and the evacuation tube 132 is sealed, the container 130 is placed in the hot isostatic press 46 which is then operated in a manner similar to that described above. Preferably, the temperature will fall within the range of 400°–440° F. while the pressure will be greater than between 5000 psi and 7500 psi, and most preferably greater than 7500 psi. As a result, the porous coated pads 128 are relatively securely attached to the biocompatible component 126.

The principles of the present invention described broadly above will now be described with reference to the following specific example, without intending to restrict the scope of the present invention.

EXAMPLE 1

Polyethylene powder having a molecular weight of approximately 3 million and conforming to ASTM F 648-84 is introduced into a first container formed from polyurethane of approximately 6 inches in diameter, 18 inches in length, and of approximately one-half inch wall thickness. The first container is substantially sealed and substantially evacuated, and is then placed in the cold isostatic press 32. The cold isostatic press is then closed, and the pressure therein is increased by introducing pressurized water into the pressure vessel to approximately 1500 psi over approximately a 2 minute period. The pressure is then maintained within the cold isostatic press for approximately 1 minute, and is then decreased to atmospheric pressure over approximately a 10 minute period. The cold isostatic press is then opened and the first container is removed and opened to reveal a cylindrical incompletely consolidated stock of dimensions 5½ inches in diameter and 14 inches in length.

The incompletely consolidated stock is then placed in a second container. The second container is formed from an aluminum foil layer with a polyester vapor barrier on its external surface and a heat-sealable, low density polyethylene layer on its internal surface. In addition, the second container is approximately 18 inches in length, 12 inches in width and has a wall thickness of 2–3 mils. The second container is then evacuated and sealed. The second container is then placed in the hot isostatic press and then the hot isostatic press is closed. The temperature of the hot isostatic press is then increased from room temperature to 400° F. over approximately a 1 hour period. At the same time, pressurized argon gas is introduced into the pressure chamber of the hot isostatic press to increase the internal pressure from atmospheric pressure to 10,000 pounds per square inch over approximately a 3 hour period. After reaching 400° F. and 10,000 psi, the temperature and pressure within the hot isostatic press are maintained for approximately 5 hours. The temperature is then allowed to decrease to 100° F. over approximately a 4 hour period. At the same time, the pressure within the hot isostatic press is decreased to atmospheric pressure over a 30 minute period. After release of the pressure and cooling to room temperature, the hot isostatic press is opened and the second container is removed. The second container is then opened to reveal a relatively completely consolidated stock which resembles a cylinder having dimensions of 4 inches in diameter and 12 inches in length. The relatively completely consolidated stock is tested to have a crystallinity of 45%–60%. The consolidated stock is subsequently machined to form a tibial bearing which is then packaged and then exposed 2.5 megarads of radiation from a cobalt source for sterilization.

EXAMPLE 2

Two portions of polysulfone approximately 5 mils in thickness are vacuum formed into a shape which resembles each half of a biocompatible component in the form of a hip joint prosthesis described above. Each portion of the polysulfone representing the halves of the biocompatible component is then placed in a stainless steel container with continuous carbon fibers disposed between the portions. The container is placed in the hot isostatic press and then the hot isostatic press is closed. The temperature of the hot isostatic press is then increased from room temperature to approximately 410° F. over approximately a one hour period. At the same time, pressurized argon gas is introduced into the pressure chamber of the hot isostatic press to increase the internal pressure from atmospheric pressure to 7500 psi over approximately a three-hour period.

After reaching 410° F. and 7500 psi, the temperature and pressure within the hot isostatic press are maintained for approximately a thirty minute period. The temperature is then allowed to decrease to room temperature after which the pressure is released. After the pressure has been released and the hot isostatic press has been cooled to room temperature, the hot isostatic press is opened and the container is removed. The container is then opened to reveal a biocompatible component in which the polysulfone has encapsulated the carbon fibers.

EXAMPLE 3

A biocompatible component in the form of a hip joint prosthesis described above is initially formed from continuous carbon fibers which are encapsulated by polysulfone. Methylene chloride is applied to the upper portion of the biocompatible component so as to partially dissolve the polysulfone. After portions of the polysulfone have been melted, a plurality of porous coated pads described above are applied to the region of the biocompatible component to which methylene chloride is applied. The biocompatible component with the porous coated pads attached is then placed in a stainless steel container of the type described above which is then filled with zirconium oxide beads. After the container is evacuated and sealed, the container is placed in a hot isostatic press and then the hot isostatic press is closed.

The temperature of the hot isostatic press is then increased from room temperature to approximately 410° F. over approximately a one hour period. At the same time, pressurized argon gas is introduced into the pressure chamber of the hot isostatic press to increase the internal pressure from atmospheric pressure to 5000 psi over an approximately a one hour period. After reaching 410° F. and 5000 psi, the temperature in the pressure of hot isostatic press are maintained for approximately 45 minutes. The pressure is then allowed to decrease over approximately a four-hour period, while the temperature within the hot isostatic press is decreased to ambient over a thirty minute period. After release of the pressure and cooling to room temperature, the hot isostatic press is open and the container is removed. The second container is then opened to reveal the biocompatible component with the porous coated pads relatively securely attached.

EXAMPLE 4

A biocompatible material stock in the form of a slab is placed within a stainless steel container which is then formed with zirconium oxide beads. The slab is approximately 1.5 inches thick and is 10 in length and 10 in width. After the container is then evacuated and sealed in the manner described above, the container together with the biocompatible material stock is placed in a hot isostatic press. The temperature of the hot isostatic press is then increased from room temperature to approximately 430° F. over approximately a 0.75 hour time period. At the same time, pressurized argon gas is introduced into the hot isostatic press to increase the internal pressure from atmospheric to approximately 7500 psi over approximately a one hour time period.

After reaching 430° F. and 7500 psi, the temperature and pressure of the isostatic press are maintained for approximately 0.75 hours. The temperature is then reduced to room temperature after which the pressure is released. After pressure has been released and the hot isostatic press has been cooled to room temperature, the hot isostatic press is opened and the container is removed. The container is then opened to reveal a slab of biocompatible material stock in which the voids are reduced.

EXAMPLE 5

A biocompatible component in the form of a stem of a hip joint prosthesis described above is initially formed from carbon fibers which are encapsulated by a polysulfone. The biocompatible component is then ultrasonic cleaned in water to remove surface containments. The biocompatible component is then subjected to a grit blasting operation. In this regard, the portions of the biocompatible component which are not to receive the porous coating are initially covered with polyvinyl chloride tape. The biocompatible component is then placed in front of grit blaster operating at 40 psi with a ½ inch nozzle using a 16 grit silicon carbide particles. By grit blasting the biocompatible component, a roughen surface is formed in the region which is exposed to the particles. The polyvinyl chloride tape is then removed from the biocompatible component.

It will be appreciated that other means may be used for obtaining a roughened surface on the biocompatible component. For example, a 1/16" drill bit may be used to form the roughened surface. In this regard, the drill bit may be randomly disposed against the portion of the biocompatible component where the roughened surface is to be formed thereby generating a plurality of holes. This process is continued until the desired surface roughness is obtained. A dove-tail cutter may also be used to form the roughened surface. In this regard, a dove-tail cutter having a cutting surface of a maximum of 1/32" in diameter may be disposed against the surface of the biocompatible component which is to be roughened and then the axis of rotation of the cutter is moved in a circular fashion. The dove-tail cutter is then removed from the biocompatible component and then disposed against another portion of the surface of the biocompatible component. This process is repeated until the desired surface roughness is obtained.

The biocompatible component is then cleaned in a second ultrasonic cleaning operation. The portions of the biocompatible component which are not to receive the porous coating are then covered with heat tape which is resistant to the high temperature which are to be generated during the plasma spray operation. Care is taken so that the portions of the biocompatible component which are covered by the porous coating are not physically contacted after the second ultrasonic cleaning operation until the porous coating is applied. In this regard, the storage rack which is used to transport the biocompatible component to the plasma spray chamber supports the biocompatible component only at those areas which are not to be coated with porous coating.

The biocompatible component is then placed in a plasma spray chamber in such a manner that portions of the biocompatible component which receives the porous coating is not touched. The spray chamber is initially evacuated to approximately 10 millitorr and then backfilled with argon gas to a pressure slightly above atmospheric. The plasma spray is then applied to the biocompatible component for a period of approximately 20 seconds. After the plasma spray has been applied for this period of time, the biocompatible component is placed in front of the exhaust fan of the spray chamber for approximately 1 minute. This process of applying the plasma spray and then cooling the biocompatible component is repeated approximately 8 times. The biocompatible component is then removed from the spray chamber and then sandpaper is used to remove loose material from the biocompatible component. The biocompatible component is washed in a water jet operating at 900 psi to remove additional residue.

The biocompatible component is then placed in a stainless steel container of the type described above which is then filled with zirconium oxide beads. The container is then evacuated and sealed. The container, together with the biocompatible component, is then placed in a hot isostatic press and then the hot isostatic press is closed. The temperature of the hot isostatic press is then increased from room temperature to approximately 430° F. and while the pressure is increased to 7500 psi. The temperature and pressure of the hot isostatic press are maintained for approximately 45 minutes. The temperature of the hot isostatic press is then allowed to cool to approximately 100° F. over a one hour time period and then the pressure of the hot isostatic press is decreased to atmospheric over a thirty-minute time period. The hot isostatic press is then cooled to room temperature after which the hot isostatic press and the container is removed. The container is then opened to reveal a biocompatible component with the porous coated surface relatively securely attached.

It will be appreciated that the foregoing description of the preferred embodiment of the invention is presented by way of illustration only and not by way of any limitation. For example, a preheating step may be used to preheat the incompletely consolidated stock prior to placing the consolidated stock in the hot isostatic press. In addition, the various containers may be of different sizes and of different materials. Furthermore, filters such as paper towels may be located within the various evacuation tubes. Various alternatives and modifications may be made to the illustrative embodiment without departing from the spirit and scope of the invention.

What is claimed is:

1. A biocompatible component resistant to wear fabricated from a substantially consolidated stock of material, said biocompatible component formed by the steps of:

preparing said substantially consolidated stock from an ultra high molecular weight polyethylene powder by:

(a) subjecting said powder to a cold isostatic pressure treatment thereby forming an incompletely consolidated stock from said powder, (b) subjecting said incompletely consolidated stock to a hot isostatic pressure treatment to form said substantially consolidated stock from said incompletely consolidated stock while controlling crystallinity so as to substantially avoid increasing the crystallinity of the substantially consolidated stock above that of the powder; and machining said substantially consolidated stock to form said biocompatible component.

2. The biocompatible component according to claim 1, wherein said step of subjecting said powder to a cold isostatic pressure treatment includes the steps of:

placing said powder into a first flexible container; and subjecting said first flexible container to a pressure sufficient to form said incompletely consolidated stock.

3. The biocompatible component according to claim 2, wherein said step of placing said powder into a first flexible container includes the steps of:

placing said powder in a substantially cylindrical container formed from polyurethane.

enclosing said substantially cylindrical container with a plug; and evacuating and sealing said substantially cylindrical container.

4. The biocompatible component according to claim 2, wherein said step of subjecting said incompletely consolidated stock to a hot isostatic pressure treatment includes the steps of:

placing said incompletely consolidated stock into a second flexible container; and subjecting said second flexible container to a sufficient pressure and temperature so as to form said substantially completely consolidated stock.

5. The biocompatible component according to claim 4, wherein said step of placing said incompletely consolidated stock into a second flexible container includes the step of placing said incompletely consolidated stock in a foilized heat sealable container formed from a layer of aluminum foil, a polyester vapor barrier, and a heat sealable layer.

6. The biocompatible component according to claim 5, wherein said step of placing said incompletely consolidated stock into a second flexible container includes the steps of:

substantially enclosing said second flexible container; and substantially evacuating said second flexible container.

* * * * *

UNITED STATES PATENT AND TRADEMARK OFFICE
CERTIFICATE OF CORRECTION

PATENT NO.  : 5,466,530
DATED       : November 14, 1995
INVENTOR(S) : Garry L. England and Joel C. Higgins It is certified that error appears in the above-indentified patent and that said Letters Patent is hereby corrected as shown below:

On the Title Page, under Attorney, Agent, or Firm, "Harness, Dickey & Pierce" should be --Harness, Dickey & Pierce, P.L.C.--;

Column 2, Line 3, "ultrahigh" should be --ultra-high--;

Column 3, Line 8, after "Fig. 5" insert --is a perspective view--;

Column 6, Line 5, before "inches" insert --6--;

Column 6, Line 16, "deairing" should be --de-airing--;

Column 8, Line 10, delete "and" and insert --,-- after "108" (first occurrence);

Column 8, Line 22, "consolidate" should be --consolidated--;

Column 8, Line 33, "hours" should be --hour--;

Column 11, Line 26, in "Ti-6Al-4V", the "l" should be a small letter "l", not a number 1;

Column 11, Line 32, "are" should be --is--;

UNITED STATES PATENT AND TRADEMARK OFFICE
CERTIFICATE OF CORRECTION

PATENT NO. : 5,466,530
DATED : November 14, 1995
INVENTOR(S) : Garry L. England and Joel C. Higgins It is certified that error appears in the above-indentified patent and that said Letters Patent is hereby corrected as shown below:

Column 15, Line 11, delete "and";

Column 16, Line 19, Claim 3, "." should be --;--.

Signed and Sealed this

Twenty-sixth Day of August, 1997

*Attest:*

BRUCE LEHMAN

*Attesting Officer*     Commissioner of Patents and Trademarks